United States Patent [19]

Fleming

[11] Patent Number: Plant 7,425

[45] Date of Patent: Jan. 22, 1991

[54] KALANCHOE PLANT NAMED SMALL WONDER

[75] Inventor: Margaret M. Fleming, Soquel, Calif.

[73] Assignee: The Plant Company, Soquel, Calif.

[21] Appl. No.: 422,086

[22] Filed: Oct. 16, 1989

[51] Int. Cl.[5] ..... A01H 5/00
[52] U.S. Cl. ..... Plt./68
[58] Field of Search ..... Plt./68

*Primary Examiner*—Howard J. Locker
*Attorney, Agent, or Firm*—Foley & Lardner, Schwartz, Jeffery, Schwaab, Mack, Blumenthal & Evans

[57] ABSTRACT

A Kalanchoe plant named Small Wonder particularly characterized by its orange-red flower color with red highlights; flower diameter of 14 to 16 mm at maturity; flowering response of from 10 weeks in summer to 12 weeks in winter after start of short days; very floriferous habit with excellent display of many flowers; excellent keeping quality of flowers and foliage; foilage always small, medium green, nicely serrated and lobed; free branching with or without pinching; compact plant habit with intermediate vigor; responsive to B-9 applications to reduce internode length and peduncle elongation; and adaptable to pot sizes from 10 to 15 cm.

2 Drawing Sheets

The present invention relates to a new and distinctive cultivar of Kalanchoe plant, botanically known as *Kalanchoe blossfeldiana* Poelln., and referred to by the cultivar name Small Wonder.

Small Wonder, identified as 409-021, is a product of a planned breeding program which had the objective of creating new Kalanchoe cultivars for year-round commercial production, with earlier flowering response, good branching yet compact flowering plants, suitable for flowering in pots ranging from 10 to 15 cm, and with good flower and foliage keeping quality.

Small Wonder was originated from a cross by the inventor Margaret M. Fleming in a controlled breeding program in Half Moon Bay, Calif., in 1983.

The female parent of Small Wonder was the cultivar Eternity, disclosed in U.S. Plant Pat. No. 5,253. The male parent was the cultivar Regulus, disclosed in U.S. Plant Pat. No. 4,817.

Small Wonder was discovered and selected by the inventor as one flowering plant within the progeny of the stated cross in September, 1984 in a controlled environment in Half Moon Bay, Calif.

The first act of asexual reproduction of Small Wonder was accompilshed when vegetative cuttings were taken by the inventor from the initial selection in January, 1985 in a controlled environment in Half Moon Bay, Calif.

Horticultural examination of controlled flowerings of successive plantings has shown that the unique combination of characteristics as herein disclosed for Small Wonder are firmly fixed and are retained through successive generations of asexual reproduction. Small Wonder has not been observed under all possible environmental conditions. The phenotype may vary significantly with variations in environment such as temperature, light intensity and daylength.

The following observations, measurements and comparisons described plants grown in Soquel, Calif., under greenhouse conditions which approximate those generally used in commercial greenhouse practice.

The following traits have been repeatedly observed and are determined to be basic characteristics of Small Wonder, which, in combination, distinguish this Kalanchoe as a new and distinct cultivar:

1. Orange-red flower color with red highlights.
2. Flower diameter of 14 to 16 mm at maturity.
3. Flowering response of from 10 weeks in summer to 12 weeks in winter after start of short days.
4. Very floriferous, with excellent display of many flowers.
5. Excellent keeping quality of flowers and foliage.
6. Foliage always small, medium green, nicely serrated and lobed.
7. Branches freely with or without pinching.
8. Compact plant habit with intermediate vigor.
9. Responds well to B-9 applications to reduce internode length and peduncle elongation.
10. Proper scheduling makes this new cultivar suitable for production in 10 cm to 15 cm pots.

The accompanying photographic drawings show typical inflorescence and leaf characteristics of Small Wonder, with colors being as nearly true as possible with illustrations of this type. Sheet 1 is a color photograph of Small Wonder grown as a non-pinched flowering Kalanchoe in a 10 cm pot. Although the leaf edges appear to have a dark or reddish tone, this is a photographic imperfection and not a characteristic of Small Wonder. Sheet 2 is a black and white photograph showing the leaves of Small Wonder at three stages of development (mature, intermediate and immature).

Of the commercial cultivars known to the inventor, none are suitable for comparison with Small Wonder. The orange-red flower color with red highlights is unique. The foliage is different from any known variety: medium green, nicely serrated and lobed, with excellent keeping quality. However, flowering response, productivity, plant habit, responsiveness to B-9 applications, and adaptability to various pot sizes of Small Wonder compares with the cultivar Fascination, disclosed in U.S. Plant Pat. No. 5,889.

When compared to the female parent Eternity, Small Wonder is more vigorous, and its foliage is much smaller, less fleshy and a lighter green in color. The leaf lobes of Small Wonder are unique. Small Wonder blooms 1–3 weeks earlier than Eternity, branches much more freely than Eternity (or any other cultivar known to the inventor), and has as good or better keeping quality than Eternity, which has been the industry standard for keeping qualities ever since its introduction. A further distinction is in the substantially different shades of orange of the respective flowers.

Comparing Small Wonder to its male parent Regulus, Small Wonder is more vigorous and its foliage is lobed in a distinctive way, is less fleshy, and is a lighter green color and much more durable. Regulus, which has a beautiful orange flower color when grown well, tends toward foliage degradation and an oversensitivity to salt buildup and overwatering which makes the root system susceptible to damage. Small Wonder did not inherit these weaknesses from Regulus.

In the following description color references are made to The Royal Horticultural Society Colour Chart. The color values were determined on plant material grown as a non-pinched pot plant in a 10 cm pot in Soquel, Calif., on Oct. 23, 1988.

Classification:

*Botanical.*—*Kalanchoe blossfeldiana* Poelln. cv. Small Wonder.

*Commercial.*—Flowering pot Kalanchoe.

Parentage:

*Female parent.*—Eternity (U.S. Plant Pat. No. 5,253).

*Male parent.*—Regulus (U.S. Plant Pat. No. 4,817).

Propagation:

(A) *Type cutting.*—Short tip cutting, with stems up to 2 cm.

(B) *Time to root.*—10 days at 21° C. in summer, 14 days at 21° C. in winter.

(C) *Rooting habit.*—Many very fine roots, fibrous.

Plant description:

(A) *Form.*—Compact, upright growth with intermediate vigor. Growing and scheduling practices can produce a small plant in a 10 cm pot up to a larger plant in a 15 cm pot.

(B) *Habit of growth.*—Rate of growth moderate for this type of plant. Generally, shoots are formed at every node. Internode length of natural vegetative plant, 12–25 mm.

(C) *Height.*—Short to medium; 13–18 cm. above a 10 cm. pot, with 1–3 applications of 3500 ppm B-9 SP linear growth regulator.

(D) *Foliage description.*—Leaves simple, opposite, deeply lobed and nicely serrated. 1. Size: Always small; average full grown leaf in a 10 cm flowering pot is 80 mm long×43 mm wide. 2. Shape: Ovate to elliptic, apex obtuse to pointed, base attenuate. 3. Texture: Glabrous, coriaceous, succulent. 4. Margin: Sinuate to crenate. 5. Color: Mature foliage: Upper surface 137B. Under surface 137B to 137C. 6. Durability: Excellent; no degradation observed even on the lower foliage of plants retained for months beyond normal expectancy.

Flowering description:

(A) *Flowering habit.*—Inflorescence of each shoot is formed by dichotomous branching, starting with opening of terminal flower of main axis, followed by terminal flowers of the side branches, continuing with subsequent development of branches in the inflorescence. Opening of new buds (10–15 mm. in length) will continue for two months or more. Individual flowers last two weeks or more after opening.

(B) *Flowering response.*—Flowering time under controlled daylength after start of short days is 10 weeks in summer to 12 weeks in winter.

(C) *Flowers borne.*—Compound dichasial cymes; peduncle length is 5–10 cm. in length and 3–7 mm. in diameter, depending on growing conditions and application of growth regulator; pedicels 4–6 mm. in length and approximately 1 mm. in diameter.

(D) *Quantity of flowers.*—Very floriferous; flowers on both main axis and side laterals, typical floret count of 100 or more per major inflorescence and 500 or more total per plant in a 10 cm. pot grown in accordance with commercial culture practices, with 4 to 6 side laterals in a 10 cm pot.

(E) *Petals.*—1. Shape: Slightly pointed to almost round. 2. Color: Upper surface: Base 33C, highlighted with 40C to 40D. Under surface: Base 29C, slightly streaked with 40D. 3. Number of petals: 4, united in corolla. 4. Flower diameter: 14 to 16 mm at maturity.

(F) *Reproductive organs.*—1. Stamens: 8 in number. a. Anther shape: Flat, elliptical, color yellow. b. Filament color: Light green. c. Pollen color: Yellow. 2. Pistils a. Stigma shape: Flat, crystalline, color greenish white. b. Style color: Light green. c. Ovaries: 4-celled, color light green.

(G) *Keeping quality.*—Excellent; flowers last two weeks or more, with the plant being in flower two months or more.

Disease resistance: Small Wonder is resistant or immune to the foliar disease Powdery Mildew, and no occurrences of chlorosis, necrotic spot, tip die-back, root rot, or stem rot have been observed. Small Wonder is also resistant or immune to the flower disease Botrytis, and no fading or color breaking has been observed.

Fragrance: None perceived in flowers or foliage.

I claim:

1. A new and distinct plant of Kalanchoe named Small Wonder, as described and illustrated.

* * * * *

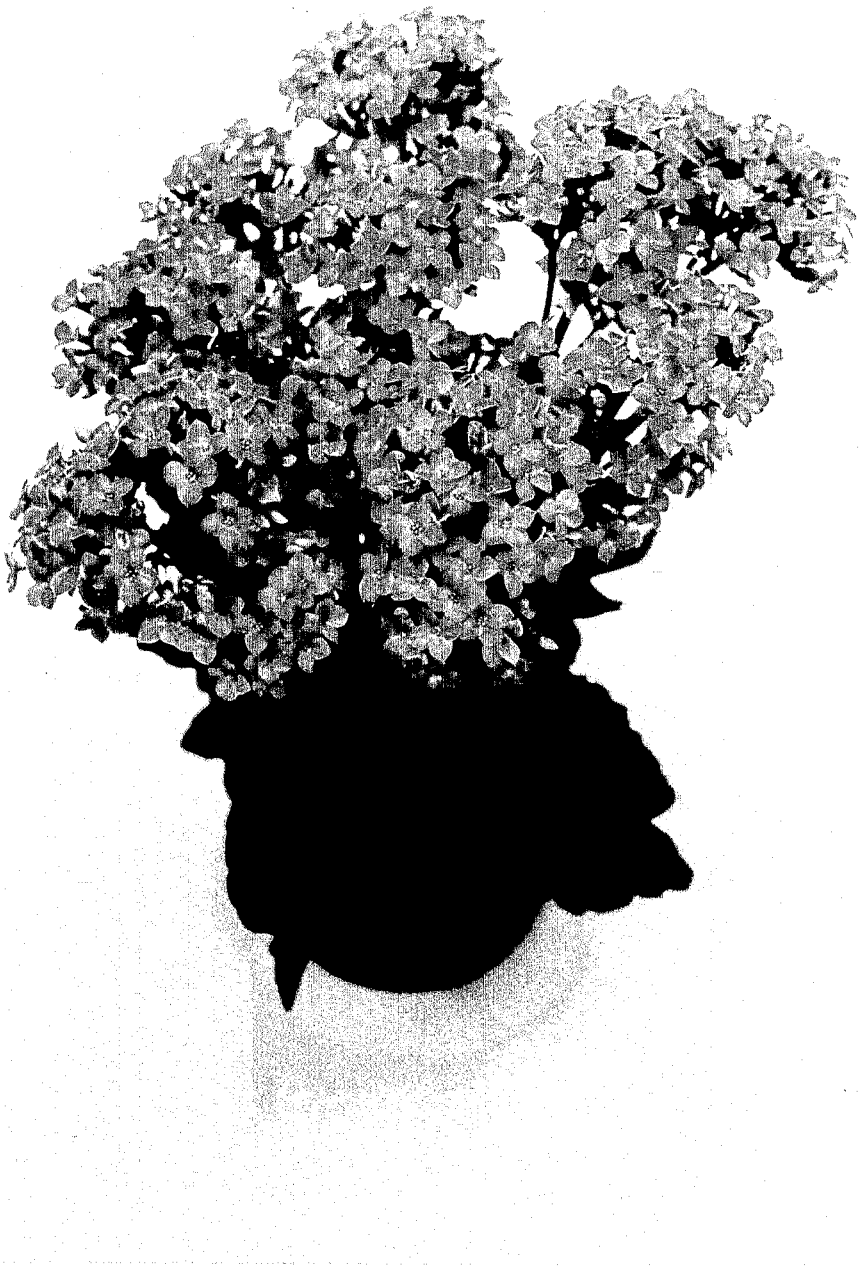

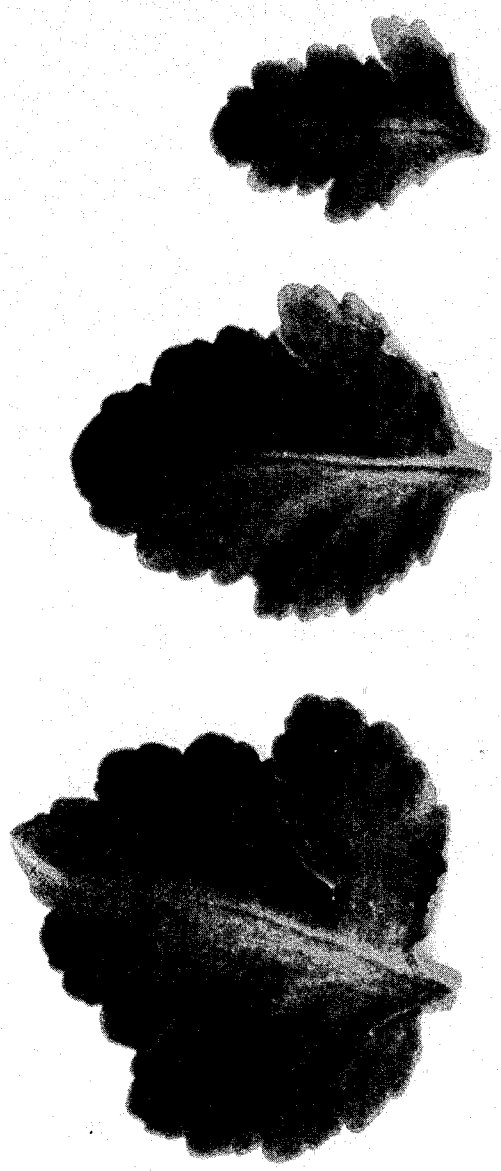
SMALL WONDER